(12) United States Patent
Yazawa et al.

(10) Patent No.: US 6,280,621 B1
(45) Date of Patent: *Aug. 28, 2001

(54) BLOOD FILTER CARTRIDGE WITH OVERFLOW RECEIVER

(75) Inventors: Kenichiro Yazawa; Takaki Arai; Osamu Seshimoto, all of Saitama (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/487,679

(22) Filed: Jan. 19, 2000

(30) Foreign Application Priority Data

Jan. 19, 1999 (JP) .................................. 11-010046

(51) Int. Cl.⁷ ......................... B01D 29/05; B01D 29/56; B01D 29/92
(52) U.S. Cl. .......................... 210/248; 210/445; 210/451; 210/477; 210/489; 210/503; 73/863.23; 422/101
(58) Field of Search ............................. 210/248, 321.6, 210/321.65, 435, 445, 446, 449, 451, 488, 489, 500.21, 503, 477; 73/863.23; 422/101

(56) References Cited

U.S. PATENT DOCUMENTS

| | | | |
|---|---|---|---|
| 3,481,477 | * | 12/1969 | Farr . |
| 3,640,393 | * | 2/1972 | Hurtig . |
| 3,693,804 | * | 9/1972 | Grover . |
| 3,819,055 | * | 6/1974 | Skinner . |
| 4,279,863 | * | 7/1981 | Friehler . |
| 4,487,696 | * | 12/1984 | Ferrara . |
| 4,522,713 | * | 6/1985 | Nussbaumer et al. . |
| 5,215,920 | * | 6/1993 | Lyman et al. . |
| 5,306,420 | * | 4/1994 | Bisconte . |
| 5,571,412 | * | 11/1996 | Nerli . |
| 5,979,669 | * | 11/1999 | Kitajima et al. . |
| 5,996,811 | * | 12/1999 | Kitajima et al. . |

\* cited by examiner

*Primary Examiner*—Duane Smith
*Assistant Examiner*—Fred Prince
(74) *Attorney, Agent, or Firm*—Reed Smith LLP

(57) ABSTRACT

The blood filter cartridge of the invention can be used as a sample cup of an analyzer without sucking bubbles, which comprises a blood filtering material, a holder containing the blood filtering material and having a blood inlet and a filtrate outlet, and a filtrate receiver for receiving filtrate discharged from the filtrate outlet, the filtrate receiver has an upper end having a difference in height or structure for returning the filtrate from the upper end of the filtrate receiver to the filtrate outlet.

13 Claims, 3 Drawing Sheets

BLOOD FILTER CARTRIDGE WITH OVERFLOW RECEIVER

BACKGROUND OF THE INVENTION

This invention relates to a blood filter cartridge for the preparation of a plasma or serum sample from whole blood.

The type or concentration of blood components, such as metabolites, proteins, lipids, electrolytes, enzymes, antigens, and antibodies, is measured, in general, using a plasma or serum sample obtained by centrifuging whole blood. However, centrifuging takes labor and time. Particularly, centrifuging is unsuitable for an urgent case of measuring a small number of samples promptly and in site inspection, because of requiring a centrifuge and electricity. Thereupon, it has been investigated to separate serum from whole blood by filtration.

Several filtration methods using glass fiber filter have been developed wherein whole blood is charged into the glass fiber put in a column from one side of the column, and pressurized or evacuated to obtain plasma or serum from the other side (Japanese Patent KOKOKU Nos. 44-14673, 5-52463, Japanese Patent KOKAI Nos. 2-208565, 4-208856).

However, practical filtration methods capable of obtaining an amount of plasma or serum from whole blood necessary for measuring by an automatic analyzer have not been developed except a part of items, such as blood sugar.

On the other hand, the inventors developed a blood filter cartridge composed of a filter holder and a syringe. The filter holder is composed of a holder body which contains filter material and a cap which is screwed on the holder body. The filter material consists of, e.g. two sheets of glass fiber filter, one sheet of cellulose filter and one sheet of polysulfone microporous membrane (FIG. 1 of EP 785430 A1)

Another blood filter cartridge composed of a holder body and a cap was also developed. The holder body consists of a filtrate receiver located on the upper side and a filter chamber located on the underside. The filter material put in the filter chamber is composed of six sheets of glass fiber filter and one sheet of polysulfone microporous membrane (Example 1 of EP 785012A1).

The inventors further developed various blood filter cartridges, and their patent applications were made (Japanese Patent KOKAI 10-227788, 10-185909, 10-185780, etc.)

SUMMARY OF THE INVENTION

Incidentally, the inventors conceived to use the filtrate receiver of the above blood filter cartridges as a sample cup of analyzers. They found that, when the filtrate receiver of the blood filter cartridge was used as the sample cup, the volume drawn by a suction nozzle of the analyzer varied by sucking bubbles together with the filtrate in the receiver. That is, the space in the blood filtering material, filtrate passages, and the like are filled with air. Upon filtering blood, the air is entrapped in the filtrate, and enters the filtrate receiver as bubbles. The bubbles are stable, and are not extinguished for a considerably long period. Then, the bubbles are sucked together with the filtrate by the analyzer, and cause the short volume of plasma samples.

An object of the invention is to provide a simple and inexpensive means for removing the suction of bubbles contained in the plasma or serum upon sucking a sample for analysis from the filtrate receiver of a blood filter cartridge which filters blood to receive the filtrate which is plasma or serum in the receiver which can be used as a sample cup for an analyzer.

The inventors investigated eagerly in order to solve the above bubble suction problem, and developed a means for collecting bubbles on the periphery by forming a meniscus in the filtrate receiver, or providing a difference in height on the upper end of the filtrate receiver to render the highest position of liquid level on the upper end of the receiver, and thereby, succeeded in avoiding the suction of bubbles.

Thus, the present invention provides a blood filter cartridge which comprises a blood filtering material, a holder containing the blood filtering material and having a blood inlet and a filtrate outlet, and a filtrate receiver for receiving filtrate discharged from the filtrate outlet, has a volume greater than a designed volume of the filtrate, the filtrate receiver has an upper end having a difference in height, or which has a structure for returning the filtrate from the upper end of the filtrate receiver to the filtrate outlet.

Figure 1:
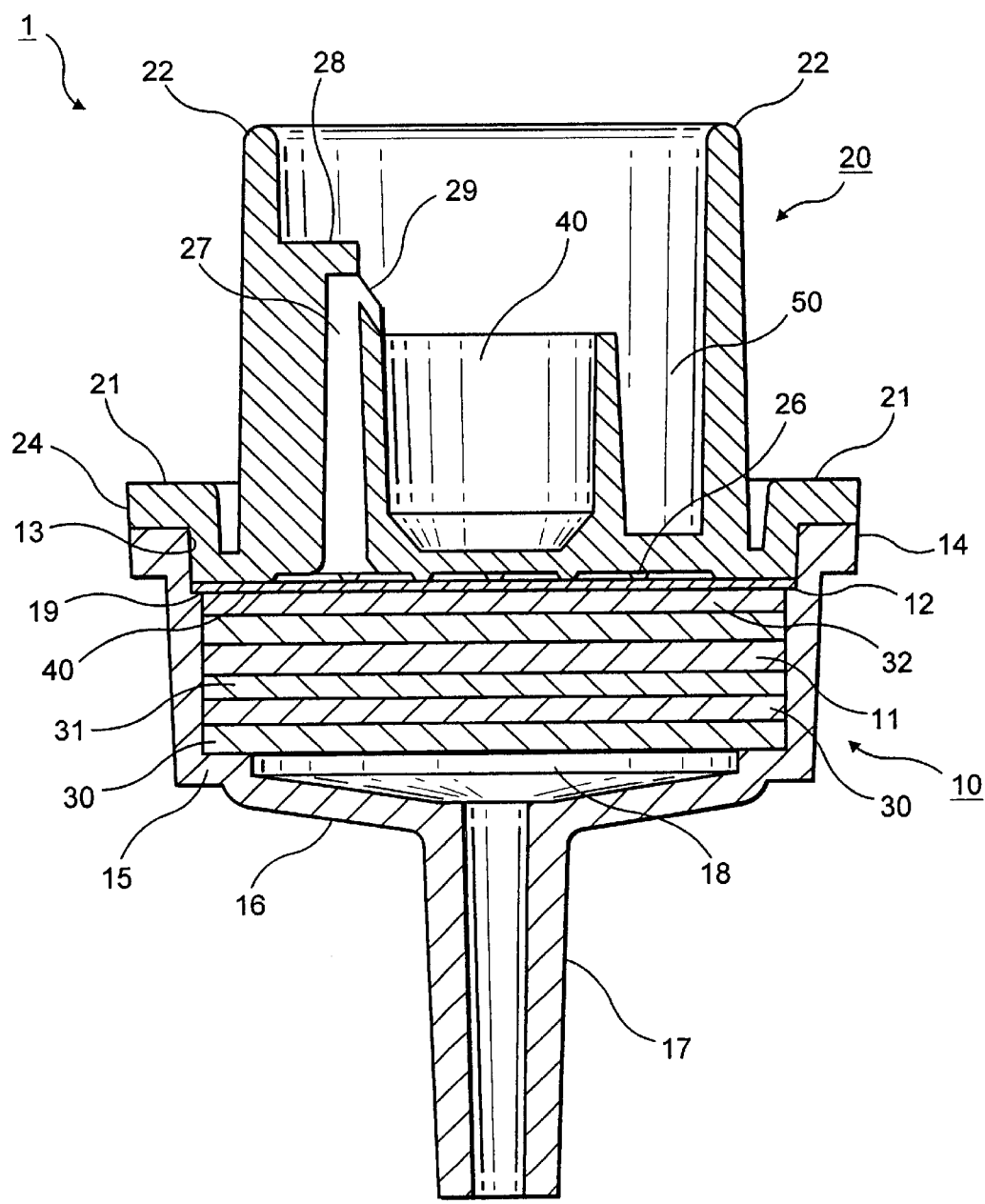
FIG. 1 is a longitudinal section of a blood filter cartridge of the invention..

1. Blood filter cartridge
10. Holder body
11. Glass fiber filter chamber (blood filter chamber)
12. Microporous membrane chamber (blood filter chamber)
13. Inclined portion
14. Flange
15. Fiber filter-placing portion
16. Funnel-shaped disc portion
17. Blood inlet
18. Space
19. Step portion
20. Cap
21. Outer wall
22. Inner wall
23. Pair of faces facing each other
24. Flange
25. Rib
26. Projection
27. Filtrate passage
28. Pent roof
29. Filtrate outlet
30. Blood filtering material
31. Glass fiber filter
32. Polysulfone microporous membrane
40. Filtrate receiver
50. Overflow receiver

DETAILED DESCRIPTION OF THE INVENTION

Although the type of the blood filtering material is not limited, in the filtering material of the invention, it is thought that the filter material to be used does not trap blood cells only by the surface, but catches to remove blood cells gradually by entangling at first large blood cell components and then smaller blood cell components in the space structure with permeating in the thickness direction in total of the filtering material, called the volumetric filtration or depth filtration. Preferable blood filtering material are glass fiber filter and the like, and a combination of glass fiber filter and microporous membrane is particularly preferred.

Preferable glass fiber filter has a density of about 0.02 to 0.5 g/cm$^3$, preferably about 0.03 to 0.2 g/cm$^3$, more preferably about 0.05 to 0.13 g/cm$^3$, a retainable particle size of about 0.6 to 9 μm preferably 1 to 5 μm. By treating the surface of glass fiber with hydrophilic polymer as disclosed in Japanese Patent KOKAI Nos. 2-208676, 4-208856, filtration proceeds more fast and smoothly. Lectin or other reactive reagent or modifier may be incorporated into glass fiber, or glass fiber may be treated therewith. Two or more glass fiber filters may be superimposed.

It is also possible that a glass fiber filter sheet is cut into small pieces, and packed in a holder. The thickness of glass fiber filter sheet is about 0.2 to 3 mm, usually about 0.5 to 2 mm. The glass fiber filter sheet is cut into pieces having a diameter of about 10 to 30 mm, preferably about 15 to 25 mm. The shape of the piece is not limited, and may be square, rectangle, triangle disc or the like.

Microporous membranes having blood cell-separating ability of which the surface has been made hydrophilic separate whole blood into blood cells and plasma specifically without hemolysis to the degree of substantially influencing analytical values. A suitable pore size of the microporous membrane is smaller than the retaining particle size of glass fiber filter, and is 0.2 μm or more, preferably about 0.3 to 5 μm, more preferably about 0.5 to 3 μm. The void content of the microporous membrane is preferably higher, and a suitable void content is about 40 to 95%, preferably about 50 to 95%, more preferably about 70 to 95%. Illustrative of the microporous membranes are polysulfone membrane, fluorine containing polymer membrane, etc.

Preferable microporous membranes are polysultone membrane, cellulose acetate membrane, and the like, and particularly preferred one is polysulfone membrane. In the blood filtering material of the invention, the glass fiber filter is located on the blood inlet side and the microporous membrane is located on the filtrate outlet side. The most preferable blood filtering material is a combination of the glass fiber filter or the aggregate of extra fine fibers and polysulfone membrane laminated in this order from the blood inlet side.

A suitable thickness of the glass fiber filter varies according to the plasma volume to be recovered and density (void content) and area of the glass fiber filter. A necessary amount of plasma for analyzing plural items using dry analytical elements is 100 to 500 μl. In practical viewpoint, a glass fiber filter having a density of about 0.02 to 0.2 g/cm$^3$ and an area of 1 to 5 cm$^2$s suitable. In this case, a suitable thickness of the glass fiber filter layer is about 1 to 10 mm, preferably about 2 to 8 mm, more preferably about 4 to 6 mm. The above thickness can be made by superposing 2 to 10 sheets, preferably 3 to 8 sheets of glass fiber filter.

A suitable thickness of the microporous membrane is about 0.05 to 0.5 mm, preferably about 0.1 to 0.3 mm, and the number of the microporous membrane is usually one. However, two or more sheets of microporous membrane may be used, if necessary.

Respective layers may be integrated by joining each other using partially disposed (e.g. spots) adhesive, according to disclosures in Japanese Patent KOKAI Nos. 62-138756-8, 2-105043, 3-16651, etc.

The blood filtering material is placed in a holder having a blood inlet and a plasma outlet. The holder is, in general, formed of a body containing the blood filtering material and a cap, and each of them is provided with at least one aperture. One is used as the blood inlet, and the other is used as the filtrate outlet, optionally further as a suction port. A suction port may be provided separately in the case that the holder is rectangular and is provided with the cap on a side of the holder, both of the blood inlet and the plasma outlet may be provided on the holder body.

The volume of the filter chamber which contains the blood filtering material is necessary to be greater than the total volume of the blood filtering material both in a dry state and in a swelled state upon absorbing a sample (whole blood). When the volume of the filter chamber is smaller than the total volume of the blood filtering material, filtration does not proceed efficiently and hemolysis occurs. A suitable ratio of the volume of the filter chamber to the total volume of the blood filtering material in a dry state is, in general, 101 to 200%, preferably 110 to 150%, more preferably 120 to 140%, although the ratio varies according to the swelling degree of the filtering material. An actual volume is set depending on the necessary amount of plasma or serum, and is about 0.5 to 2.5 ml, usually about 0.6 to 2 ml, especially about 0.7 to 1.5 ml.

Besides, it is preferable that the periphery of the blood filtering material is closely fitted to the wall of the filter chamber so as not to form a bypass of whole blood without passing the filtering material.

The blood filter cartridge is made into a closed structure except the blood inlet and the plasma outlet by attaching a cap to the holder body.

As the material of the holder, thermoplastic or thermosetting plastics are preferable. Illustrative of the plastics are general-purpose plystyrene, high impact polystyrene, methacrylate resin, polyethylene, polypropylene, polyester, nylon, polycarbonate, etc. The material may be transparent or opaque.

Fitting of the cap to the holder body may be any means, such as adhesion using adhesive or fusion welding. On that occasion, either periphery of the holder body or of the cap is located on the inside, or both peripheries are butted. The fitting may be in a state of detachable utilizing screws or the like.

The shape of the blood filtering material is not restricted, but disc and polygon is preferable in view of production. By rendering the size of the blood filtering material slightly greater than the inside section of the holder body (i.e. filter chamber), breakthrough of blood at the periphery of the filtering material can be prevented. To render the shape square is preferable because of no generation of cutting loss. Moreover, cut pieces of glass fiber filter can also be served.

The filtrate receiver receives the filtrate, which is plasma or serum, discharged from the filtrate outlet, and the filtrate outlet is located above the liquid level of the filtrate receiver. The filtrate outlet may be provided on the upper part of the side wall of the filtrate receiver or a pipe standing on the inside of the filtrate receiver. The filtrate receiver is made into various shapes in connection with various factors, such as the relation to the position of sucking analytical sample, the relation to the blood filtering chamber, the relation to optional other parts, and the like, and, in general, cylindrical or square. The bottom of the filtrate receiver is flat, funnel-shaped, round or the like. The volume of the filtrate receiver is, in the case of preparation of analytical sample for dry analysis, about 100 to 900 μl, usually about 200 to 600 μl, and has a depth of about 3 to 12 mm and an inner width (diameter a side length) of about 5 to 11 mm. As to the position of the filtrate outlet, the underside of the filtrate outlet is located higher than the designed liquid level of the filtrate receiver by about 0.5 to 5 mm, usually about 1 to 2 mm. Although the volume of filtrate varies according to the hematocrit value of blood, the designed liquid level is of filtering blood having a hematocrit value of 20 to 60%. The filtrate receiver may be integrated with or separated from the holder.

The filtrate receivers attached to the prior blood filter cartridges developed by the inventors have a small capacity in order to ensure a liquid depth so as to facilitate sucking by a suction nozzle of an analyzer upon using as a sampling cup of the analyzer. Then, the filtrate receivers were designed so as to be filled with the filtrate and a part of the filtrate overflows. As a result, the surface of the filtrate rises above the upper end, and bubble are concentrated at the center. The suction nozzle of the analyzer sucks the bubbles to cause errors.

In the blood filter cartridge of the invention, at least one of the following three countermeasures is taken.

The first means is to form a meniscus on the surface of the filtrate by enlarging the capacity of the filtrate receiver greater than the designed volume of the filtrate. Thereby, the bubbles are attached to the periphery. A suitable capacity of the filtrate receiver is that the designed volume of the filtrate is about 50 to 95%, preferably 70 to 90% of the filtrate receiver, and is about 150 to 2000 μl, preferably 250 to 1000 μl more preferably 300 to 800 μl.

The second means is to provide a height difference on the upper end of the filtrate receiver, and thereby, a part of the liquid surface is elevated at the high periphery portion(s) to move bubbles there. The difference in height is able to elevate the liquid surface by the surface tension of the filtrate, and is about 0.5 to 3 mm, preferably about 1 to 2 mm. As a result of providing the difference in height, the whole shape of the upper end is oblique, curved, wave, jag or the like. A suitable number of the top portions of the upper end is 1 to 10, preferably 1 to 3.

The third means is to make the portion between the upper end of the filtrate receiver and the filtrate outlet returnable of the filtrate from the receiver to the outlet. The actual means are to provide a pair of faces facing each other having a distance capable of holding the filtrate between the filtrate outlet and the upper end of the filtrate receiver, to shorten the distance between the filtrate outlet and the upper end of the filtrate receiver, to roughen the surface between the filtrate outlet and the upper end of the filtrate receiver, to make the surface between the filtrate outlet and the upper end of the filtrate receiver hydrophilic, such as formed by a material having a great surface energy, i.e. a hydrophilic material, or the like.

In the case of providing a pair of faces facing each other, a suitable distance between the faces is 3 mm or less, preferably 2 mm or less. The pair of faces is not always necessary to be provided through the whole length between the filtrate outlet and the upper end of the filtrate receiver, but is enough to make a liquid junction therebetween.

"In the case of shortening the distance between the filtrate outlet and the upper end of the filtrate receiver, a suitable distance is 4 mm or less. By rendering the face between the filtrate outlet and the upper end of the filtrate receiver oblique, the liquid junction can be formed easier."

In the case of roughening the surface between the filtrate outlet and the upper end of the filtrate receiver, the surface can be roughened by sandblasting or satirizing of mold surface.

In the third means, a suitable returning volume is 5 to 20%, preferably 7 to 15% of the filtrate once discharged into the filtrate receiver. Two or more of the above third means may be combined.

The blood filter cartridge of the invention can be provided with an overflow receiver which receives overflow from the filtrate receiver. The overflow receiver surrounds the filtrate receiver, and a part of it may be through-shaped. In the case of providing a height difference in the upper end of the filtrate receiver, the overflow portion is restricted. Accordingly, the overflow receiver is enough to be provided there.

Heretofore, the invention is explained in the type of blood filter cartridges introducing blood from the underside of the cartridge and discharging the filtrate from the upside. However, the present invention is also applicable to the opposite type, i.e. introducing blood from the upper side of the cartridge, and discharging the filtrate from the underside.

EXAMPLES

Example 1

Figure 2:
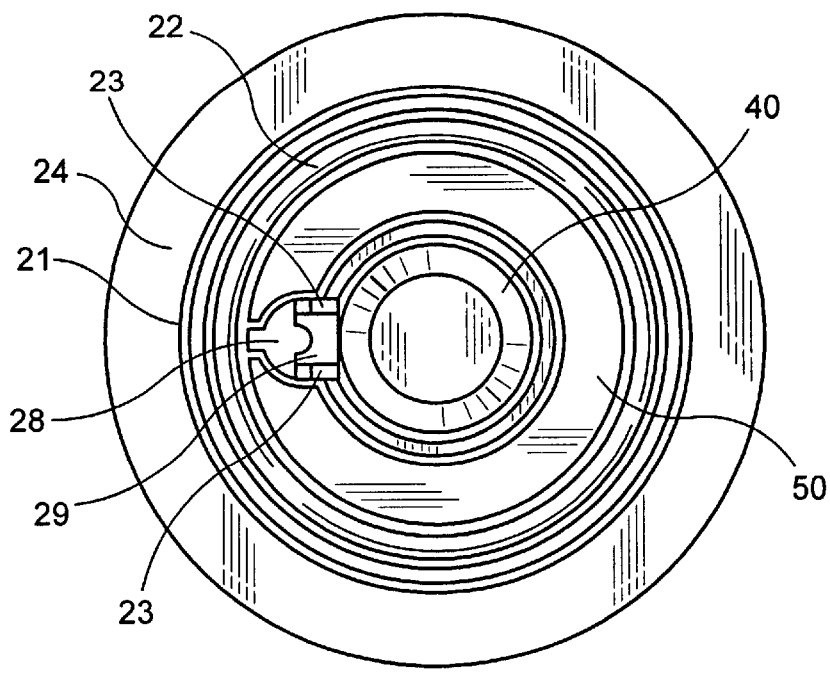
FIG. 2 is a plan view of the cap of the cartridge.
Figure 3:
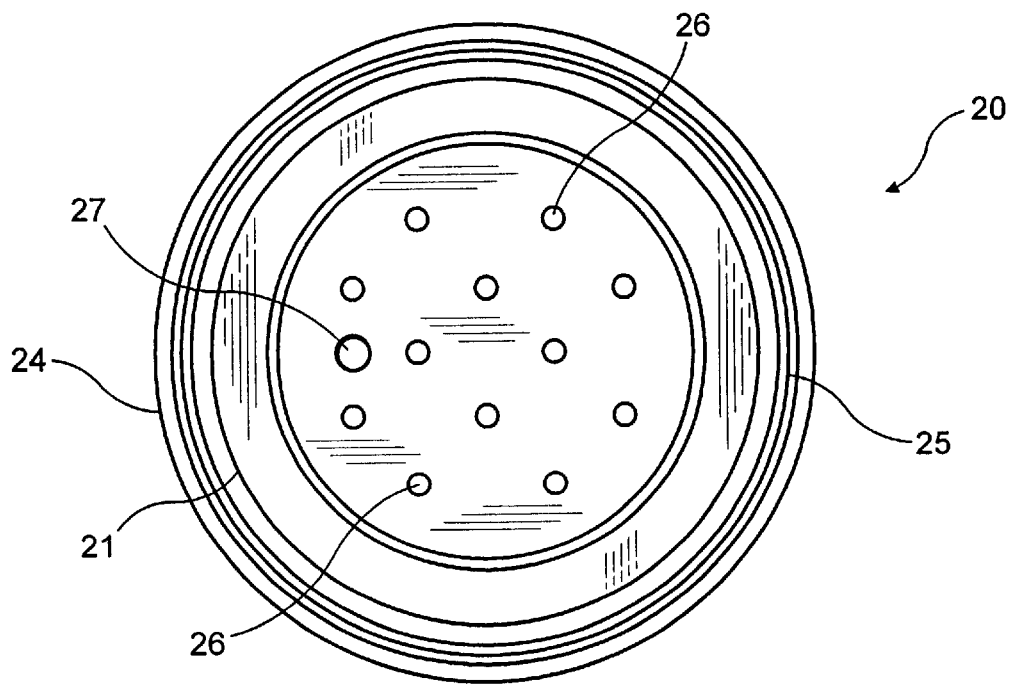
FIG. 3 is a bottom view thereof.

A blood filter cartridge of the inventors is illustrated in FIGS. 1–3. The blood filter cartridge is, as shown in FIG. 1, composed of a holder 1 consisting of a holder body 10 and a cap 20 and blood filtering material 30 consisting of a glass fiber filter 31 and a microporous membrane 32.

The holder body 10 is made of high-impact polystyrene resin, and has a glass fiber filter chamber 11 for containing the glass fiber filter 31 and a microporous membrane chamber 12 for containing a polysulfone microporous membrane as the microporous membrane 32 above the glass fiber filter chamber 11. The microporous membrane chamber 12 has a diameter greater than the glass fiber filter chamber, and the periphery of the microporous membrane 32 is nipped by the step portion 19 formed on the boundary between the glass fiber filter chamber 11 and the microporous membrane chamber 13 and the bottom of the cap 20 so as not to form a leakage without passing the blood filtering material. An inclined portion 13 which stands upward slightly obliquely is formed at the outer periphery of the step portion 19, and a flange 14 is formed outward at the upper end of the inclined portion 13.

On the other hand, the bottom of the holder body 10 is in the form of a shallow funnel, and a step portion is formed as a glass fiber filter-placing portion 15 at the periphery of the funnel-shaped disc portion 16. A nozzle-shaped blood inlet 17 is formed downward as the supply port of liquid to be filtered at the center of the funnel-shaped disc portion 16. A suction nozzle (not illustrated) is fitted to the nozzle-shaped blood inlet 17. The glass fiber filter-placing portion 15 also functions as a spacer which separates the glass fiber filter 31 from the bottom and forms a space 18 for spreading the liquid to be filtered over the whole surface of the glass fiber filter 31.

The cap 20 has an outer wall 21 and an inner wall 22 formed concentrically and a filtrate receiver 40 for storing the filtrate. An overflow receiver 50 is formed between the inner wall 22 and the filtrate receiver 40. The outer wall 21 is in the form of a taper having the same inclination angle as the inclined portion 13, and the outside diameter of the outer wall 21 is the same as the inside diameter of the inclined portion 13. That is, the outer wall 21 is fitable to the inclined portion 13 in a sealed state. A flange 24 is formed outward at the periphery of the outer wall 21, and the flange 24 is bonded to the flange 14 of the holder body 10 by ultrasonic welding. As shown in FIG. 3, a rib 25 is formed on the underside of the flange 24 so as to concentrate the ultrasonic energy there to be bonded to each other to ensure sealing. The rib 25 disappears after bonding.

As shown in FIG. 3, twelve projections 26 are formed at the bottom of the cap 20 at almost regular intervals. The projection 26 prevent the polysulfone microporous membrane 32 from adhering to the bottom.

A chimney-shaped filtrate passage 27 is formed upward penetrating the bottom of the cap 20, and a pent roof 28 is formed horizontally at the upper end of the filtrate passage 27 so as to prevent spouting of the filtrate. The pent roof 28 has the form of a combination of two half circles, as shown in FIG. 2, and the periphery of the large half circle conforms to the periphery of the filtrate passage 27. The filtrate outlet 29 of the filtrate is provide obliquely at the upper end of the filtrate passage 27, and has the form of a lower half ellipse.

As shown in FIG. 2, screens (a pair of faces) 23 are formed on both sides from the filtrate outlet 29 to the upper edge of the filtrate receiver 40 in order to prevent scattering of filtrate.

The above blood filter cartridge has a diameter of the glass fiber filter chamber 11 of 20. 1 mm and a depth thereof of 5.9 mm, a diameter of the microporous membrane chamber 12 of 21.0 mm, a diameter of the upper end of the inclined portion of 22.5 mm and a depth thereof of 2.10 mm, a diameter at the lower end of the outer periphery of the outer wall 21 of 20.98 mm and a height between the underside thereof and the flange 24 of 2.0 mm, an inside diameter of the inner wall 22 of 15.0 mm, and an inside diameter of the filtrate receiver 40 of 7.5 mm. The glass fiber filter 31 consists of six glass fiber filter sheets each having a diameter of 20.0 mm and a thickness of 0.91 mm, and the microporous membrane consists of one polysulfone microporous membrane having a diameter of 20.9 mm and a thickness of 150 $\mu$m. The filtrate outlet 29 has a longitudinal diameter of 1.3 mm and a lateral diameter of 1.2 mm. The thickness of the pent roof 28 is 1 mm, and the distance between both screens (the distance between both faces 23) is 3.0 mm.

Although the capacity of the prior filtrate receiver was 300 $\mu$l, the capacity of the filtrate receiver of the above example is 400 $\mu$l. Thereby, 300 $\mu$l of plasma discharged from the filtrate outlet 29 is received to form a meniscus on the surface.

Example

Figure 4:
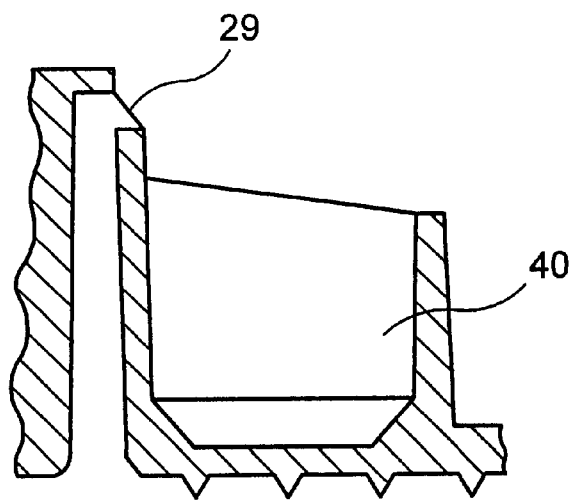
FIG. 4 is a partial section illustrating another example of the filtrate receiver.

A blood filter cartridge was prepared similar to Example 1 except that the filtrate receiver 40 was as shown in FIG. 4. The upper end (brim) of the filtrate receiver 40 is the highest at just under the filtrate outlet 29, and descend obliquely. The lowest position is opposite to the filtrate outlet 29, and the difference in height between the highest position and the lowest position is 2 mm.

Example 3

Figure 5:
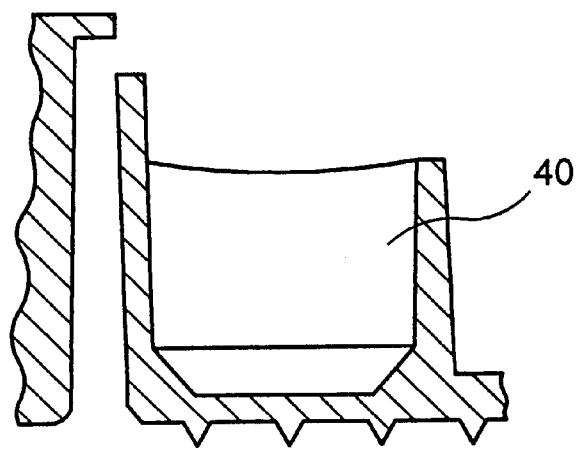
FIG. 5 is a partial section illustrating still another example of the filtrate receiver.

A blood filter cartridge was prepared similar to Example 1 except that the filtrate receiver 40 was as shown in FIG. 5. The upper end of the filtrate receiver 40 is highest at just under the filtrate outlet 29 and the opposite position and both highest positions are connected in arc, seen laterally. The lowest positions are at just the intermediate position, and the difference in height is 2 mm.

Example 4

A blood filter cartridge was prepared similar to Example 1, except that the distance between the faces 23, 23 facing each other was 2.0 mm.

What is claimed is:

1. A blood filter cartridge which comprises a blood filtering material, a holder comprising a filter chamber containing the blood filtering material and having a blood inlet and a filtrate outlet, a filtrate receiver for receiving filtrate discharged from the filtrate outlet and an overflow receiver which receives overflow from the filtrate receiver, wherein the filtrate receiver is cylindrical and located on the upside of the filter chamber and has an inside diameter effective to form a meniscus and a volume greater than a intended volume of the filtrate, and the filtrate outlet is located above a designed liquid level of the filtrate receiver.

2. The blood filter cartridge of claim 1 wherein the filtrate receiver has a capacity of 250 to 1000 $\mu$l of which 70 to 90% is the designed volume of the filtrate.

3. A blood filter cartridge which comprises a blood filtering material, a holder comprising a filter chamber containing the blood filtering material and having a blood inlet and a filtrate outlet, a filtrate receiver for receiving filtrate discharged from the filtrate outlet and an overflow receiver which receives overflow from the filtrate receiver, wherein the filtrate receiver is located on the upside of the filter chamber and has an upper end having a difference in height from the intended liquid level of the filtrate receiver and wherein the filtrate outlet is located above an intended liquid level in the filtrate receiver.

4. The blood filter cartridge of claim 3 wherein the filtrate receiver has an inner diameter of 5 to 11 mm, a depth of 3 to 12 mm and a capacity of 100 to 900 $\mu$m, and the difference in height in the liquid surface in the filtrate receiver is 0.5 to 3 mm.

5. The blood filter cartridge of claim 3 wherein the whole shape of the upper end is oblique or curved.

6. A blood filter cartridge which comprises a blood filtering material, a holder comprising a filter chamber containing the blood filtering material and having a blood inlet and a filtrate outlet, a filtrate receiver for receiving filtrate discharged from the filtrate outlet and an overflow receiver which receives overflow from the filtrate receiver, wherein the filtrate receiver is located on the upside of the filter chamber and the filtrate outlet is located above an intended liquid level of the filtrate receiver, and wherein the blood filter cartridge has a structure for returning the filtrate from the upper end of the filtrate receiver to the filtrate outlet.

7. The blood filter cartridge of claim 6 wherein the filtrate has a returning volume of 5 to 20%.

8. The blood filter cartridge of claim 7 wherein the structure for returning the filtrate from the upper end of the filtrate receiver to the filtrate outlet comprises a pair of oppression faces having a distance between them, the pair of faces capable of holding the filtrate between the filtrate outlet and the upper end of the filtrate receiver.

9. The blood filter cartridge of claim 7 wherein the structure for returning the filtrate from the upper end of the filtrate receiver to the filtrate outlet distance between the filtrate outlet and the upper end of the filtrate receiver is 4 mm or less.

10. The blood filter cartridge of claim 7 wherein the structure for returning the filtrate from the upper end of the filtrate receiver to the filtrate outlet comprises a roughened surface between the filtrate outlet and the upper end of the filtrate receiver.

11. The blood filter cartridge of claim 7 wherein the structure for returning the filtrate from the upper end of the filtrate receiver to the filtrate outlet comprises a surface between the filtrate outlet and the upper end of the filtrate receiver which is hydrophilic.

12. The blood filter cartridge of claim 3 wherein the filtrate receiver is cylindrical, and the overflow receiver surrounds the filtrate receiver.

13. The blood filter cartridge of claim 6 wherein the filtrate receiver is cylindrical, and the overflow receiver surrounds the filtrate receiver.

* * * * *